(12) United States Patent
Korc

(10) Patent No.: US 8,673,874 B2
(45) Date of Patent: Mar. 18, 2014

(54) METHODS FOR TREATING PANCREATIC CANCER

(75) Inventor: Murray Korc, Indianapolis, IN (US)

(73) Assignee: Trustees of Dartmouth College, Hanover, NH (US)

( * ) Notice: Subject to any disclaimer, the term of this patent is extended or adjusted under 35 U.S.C. 154(b) by 97 days.

(21) Appl. No.: 13/376,240

(22) PCT Filed: Jun. 8, 2010

(86) PCT No.: PCT/US2010/037716
§ 371 (c)(1),
(2), (4) Date: Dec. 5, 2011

(87) PCT Pub. No.: WO2010/144403
PCT Pub. Date: Dec. 16, 2010

(65) Prior Publication Data
US 2012/0077867 A1     Mar. 29, 2012

Related U.S. Application Data

(60) Provisional application No. 61/185,355, filed on Jun. 9, 2009.

(51) Int. Cl.
*C12N 15/11*     (2006.01)

(52) U.S. Cl.
USPC ............................................. 514/44 A

(58) Field of Classification Search
USPC .......................................... 514/44 A
See application file for complete search history.

(56) References Cited

U.S. PATENT DOCUMENTS

| | | | |
|---|---|---|---|
| 8,357,667 B2 * | 1/2013 | Korc | 514/44 A |
| 2003/0144239 A1 | 7/2003 | Agami et al. | 514/44 R |
| 2004/0181048 A1 | 9/2004 | Wang | 536/24.3 |
| 2005/0164224 A1 | 7/2005 | McSwiggen et al. | 435/6 |
| 2006/0094007 A1 | 5/2006 | Mano | 435/6 |
| 2006/0269921 A1 | 11/2006 | Segara et al. | 435/6 |
| 2007/0067865 A1 | 3/2007 | Kovalic et al. | 800/278 |
| 2007/0231304 A1 * | 10/2007 | Sobol et al. | 424/93.2 |
| 2008/0153737 A1 | 6/2008 | Lieberman et al. | 514/2 |
| 2009/0017543 A1 * | 1/2009 | Wilkes et al. | 435/456 |

OTHER PUBLICATIONS

Al-Aynati et al. (Clinical Cancer Research (2004) 10:6598-6605).*
Duxbury et al. (Journal of Biological Chemistry (2004) 279:23176-23182).*
Poch et al. "Epidermal Growth Factor Induces Cyclin D1 in Human Pancreatic Carcinoma: Evidence for a Cyclin D1-Dependent Cell Cycle Progression" Pancreas 2001 vol. 23(3): 280-287.
Saikawa et al. "Cyclin D1 Antisense Oligonucleotide Inhibits Cell Growth Stimulated by Epidermal Growth Factor and Induces Apoptosis of Gastric Cancer Cells" Japanese Journal of Cancer Research 2001 vol. 92: 1102-1109.

* cited by examiner

*Primary Examiner* — Jon E Angell
(74) *Attorney, Agent, or Firm* — Licata & Tyrrell P.C.

(57) ABSTRACT

The present invention provides a method of treating pancreatic cancer by inhibiting the activity cyclin D1 activity in tumor cells. The invention is based on the finding that cyclin D1 shRNA molecules are capable of attenuating tumor growth and interfering with tumor angiogenesis.

8 Claims, 4 Drawing Sheets

METHODS FOR TREATING PANCREATIC CANCER

This patent application is the U.S. National Stage of International Application No. PCT/US2010/037716, filed Jun. 8, 2010, which claims the benefit of priority from U.S. Provisional Application Ser. No. 61/185,355 filed Jun. 9, 2009, the contents of each of which are incorporated herein by reference in their entirety.

This invention was made with government support under Grant No. CA-101306 awarded by the U.S. Public Health Service. The government has certain rights in the invention.

BACKGROUND OF THE INVENTION

Pancreatic ductal adenocarcinoma (PDAC) is the fourth leading cause of cancer death in the United States. In spite of recent therapeutic advances, long term survival in PDAC is often limited to patients who have had surgery in early stage of the disease. The biological aggressiveness of PDAC is due, in part, to the tumor's resistance to chemotherapy and to its propensity to metastasize even when the primary tumor is small. PDAC is also characterized by a high frequency of mutations in the Kras gene, as well as by the inactivation of several tumor suppressor genes such as p16Ink4a, p53 and Smad4 (Kern, S. E. 2000. *Med. Clin. North Am.* 84:691-695). PDAC also displays abnormal upregulation of multiple mitogenic and angiogenic growth factors and their cognate high affinity receptors (Korc, M. 1998. *Surg. Oncol. Clin. N. Am.* 7:25-41). Together, these alterations serve to enhance the biological aggressiveness of PDAC.

Cyclin D1, a cell cycle regulator, is known to be overexpressed in several human cancers including PDAC (Gansauge, S. et al. 1997. *Cancer Res.* 57:1634-1637). In response to mitogenic growth factors, normal cells exhibit cyclin D1 accumulation by early to mid phase of G1. Cyclin D1 then activates its cognate cyclin dependent kinases, CDK4 and CDK6. Activated CDK4/6 initiates the phosphorylation-dependent inactivation of the retinoblastoma protein (RB) which then promotes progression through the G1-S phase of the cell cycle (Fu, M. et al. 2004. *Endocrinology* 145:5439-5447). Cyclin D1 also has CDK-independent functions (Bernards, R. 1999. Biochim. Biophys. Acta 1424:M17-M22). Thus, cyclin D1 can associate with and enhance the activity of transcription factors by recruiting cofactors that govern chromatin remodeling (Chan, H. M. et al. 2001. *Nat. Cell Biol.* 3:667-674), and contribute to the regulation of cell metabolism, differentiation and migration (Fu, M. et al. 2004. *Endocrinology* 145:5439-5447).

PDACs express high levels of cyclin D1 (Poch et al. 2001. *Pancreas* 23:280-287), and this overexpression has been correlated with decreased patient survival (Kornmann, M. et al. 1998. *Oncology* 55:363-369). Moreover, suppression of cyclin D1 expression by an antisense-based strategy resulted in marked inhibition of pancreatic cancer cell growth in vitro and in vivo (Kornmann, M. et al. 1998. *J. Clin. Invest.* 101:344-352; Yasui, M. et al. 2006. *Clin. Cancer Res.* 12:4720-4729). However, such an antisense strategy is not readily amenable for use in therapeutic regimens. RNA interference (RNAi) has rapidly become a powerful tool for gene silencing, drug discovery and target validation (Nishikura, K. 2001. *Cell* 107:415-418), and vectors that synthesize small hairpin (sh) RNA permit sustained gene silencing (Grimm, D. et al. 2007. *Am. Soc. Hematol. Educ. Program* 473-481). These vectors allow for the synthesis of 50 base pair (bp)-long single stranded RNAs that fold in 21-23 bp dsRNA with a small hairpin in the middle, and that are subsequently processed to siRNAs by the cellular machinery. These shRNA expression vectors can be engineered to contain selectable markers to generate stable transfectants, to co-express reporter genes, and to be incorporated into viral vectors such as a lentiviral vector (Hannon, G. J. et al. 2004. *Methods Mol. Biol.* 257:255-266). This virus is modified to be non-replicative, and is efficiently transduced into human cells, including non-dividing cells (Hannon, G. J. et al. 2004. *Methods Mol. Biol.* 257:255-266; Amado, R. G. and I. S. Chen. 1999. *Science* 285:674-676). It then integrates into the host genome, resulting in long-term and stable expression of the shRNA (Sikorski, R. et al. 1998. *Science* 282:1438).

U.S. Patent Application No. 2005/0164224 discloses modulating cyclin D1 expression through the use of short-interfering nucleic acid molecules, including shRNA, to treat disease such as cancer. However, the patent application fails to teach use of a lentivirus based shRNA molecule and injection directly into pancreatic tumor cells.

U.S. Patent Application 2006/0269921 discloses methods of diagnosing pancreatic cancer in a patient that involves detecting the presence of a pancreatic cancer-associated transcript, such as cyclin D1. The patent application fails to teach or suggest modulating activity of cyclin D1 to inhibit growth of cancer cells.

SUMMARY OF THE INVENTION

The present invention is a method for inhibiting growth of pancreatic cancer cells which comprises contacting pancreatic tumor cells with a replication-defective lentivirus construct expressing a cyclin D1 short hairpin RNA molecule so that growth of pancreatic tumor cells is inhibited. In certain embodiments, the pancreatic tumor cells are pancreatic ductal adenocarcinoma cells and the replication-defective lentivirus construct is injected directly into the tumor cells. In particular embodiments, the shRNA molecule is sh8-LV or sh10-LV.

Another object of the present invention is a method for decreasing tumor angiogenesis which comprises contacting pancreatic tumor cells with a lentivirus construct expressing a cyclin D1 short hairpin RNA molecule so that tumor angiogenesis is decreased. In certain embodiments, the pancreatic tumor cells are pancreatic ductal adenocarcinoma cells and the replication-defective lentivirus construct is injected directly into the tumor cells. In particular embodiments, the shRNA molecule is sh8-LV or sh10-LV.

Yet another object of the present invention is a method for treating pancreatic cancer which comprises administering to a patient diagnosed with pancreatic cancer a replication-defective lentivirus construct expressing a cyclin D1 short hairpin RNA molecule and a pharmaceutically acceptable vehicle. In one embodiment, the replication-defective lentivirus construct is injected directly into the tumor cells. In particular embodiments, the shRNA molecule is sh8-LV or sh10-LV.

These and other aspects of the present invention are set forth in more detail in the following description of the invention.

BRIEF DESCRIPTION OF THE DRAWINGS

FIG. 1 depicts results of experiments in vitro where cyclin D1 has been silenced. ASPC-1 and BxPC3 cells were either not infected (parental cells: P) or infected with the mock-infected lentivirus pll37 (E), or pll37 containing sequences encoding luciferase (L), or cyclin D1 specific shRNA 8 (8) or 10 (10), or their combination (K).

DETAILED DESCRIPTION OF THE INVENTION

Figure 1A:
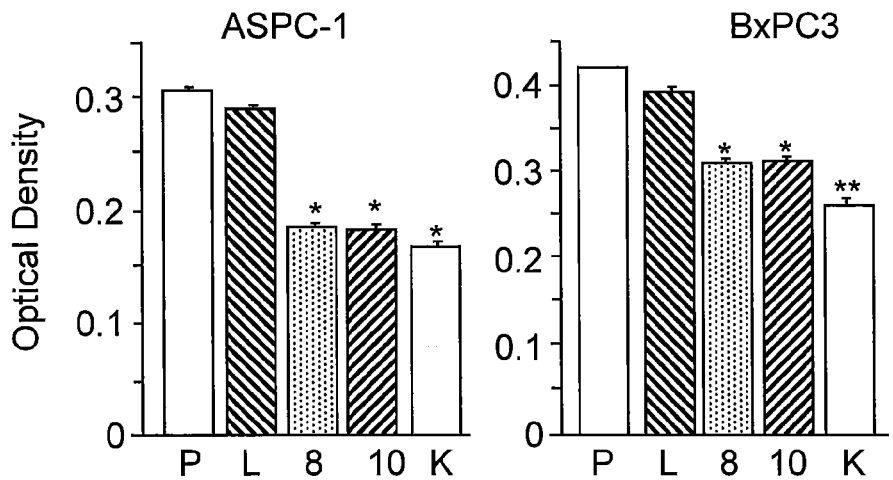
FIG. 1A shows results of anchorage-dependent growth that was determined by the MTT assay. Data are the means±SE of triplicate determinations from three independent experiments. *p<0.05, p<0.01 when compared with Luc.

It has now been found that lentiviral vectors can be used to integrate the sequence of a cyclin D1 shRNA in human pancreatic carcinoma cells, thereby allowing for stable expression of the shRNA and a sustained suppression of cyclin D1 expression in tumor cells. Further, the down-regulation of cyclin D1 expression resulted in attenuated growth of the cells in anchorage-dependent and -independent conditions, as well as decreased invasiveness in vitro. Moreover, a single intra-tumoral injection of the recombinant lentiviruses targeting cyclin D1 attenuated the growth of pre-existing tumors by decreasing cancer cell proliferation and angiogenesis. Therefore, the present invention includes compositions and methods for inhibiting growth of pancreatic cancer cells as well as compositions and methods for treating pancreatic cancer.

Experiments were performed first to develop a construct for administration. To select the shRNA sequence to be introduced into the lentivirus, a pool of different siRNA sequences directed against human cyclin D1 were tested in ASPC-1 cells. After siRNA transfection, cell lysates were subjected to immunoblotting using anti-cyclin antibodies. The siRNA pool efficiently silenced cyclin D1 expression at the protein level. Each sequence of this pool was then tested in order to select the two most efficient siRNA sequences, which were then used to design the oligonucleotides for the shRNA targeting cyclin D1. These oligonucleotides were then annealed and cloned into the pll3.7 vector.

Lentivirus infectivity was determined following infection of ASPC-1 and BxPC3 human pancreatic cancer cells with the GFP-expressing lentivirus at a multiplicity of infection (m.o.i.) of 10. Results showed that 90% of ASPC-1 and BxPC3 cells exhibited strong fluorescence, and these results were confirmed by FACS. Next, ASPC-1 and BxPC3 were infected at a different m.o.i. with shRNA-lentiviruses targeting cyclin D1. shRNA-lentiviruses targeting luciferase (shLuc-LV) were used as a control. The processing and subsequent functionality of the control shRNA were tested by infecting 293 cells that constitutively express luciferase with shLuc-LV. A decrease in luciferase activity in these cells demonstrated that the shRNA targeting luciferase is processed by the silencing pathway.

As determined by immunoblotting, shRNA sequences of sh8-LV and sh10-LV were the most effective at suppressing cyclin D1 levels in both cell lines; the combination of both sh8-LV and sh10-LV was also effective. The viruses containing sh8-LV and sh10-LV were therefore used in all subsequent experiments.

Experiments were then performed to determine the effect of cyclin D1 down-regulation on the ability of pancreatic cancer cells to proliferate and invade. Initial experiments were performed to determine the effects of cyclin D1 down-regulation on cell doubling times. Parental and mock-infected cells had similar doubling times of 31±0.5 h, whereas ASPC-1 cells infected with lentivirus expressing shRNA 8 (sh8-LV) and shRNA 10 (sh10-LV) displayed doubling times of 39 hours (p<0.05) and 40 hours (p<0.01), respectively. Similarly, parental and mock infected BxPC3 cells exhibited doubling times of 25 hours, whereas infection of these cells with sh8-LV and sh10-LV prolonged the doubling times to 34±1.4 hours (p<0.05) and 30±1.2 hours (p<0.05), respectively.

Figure 1B:
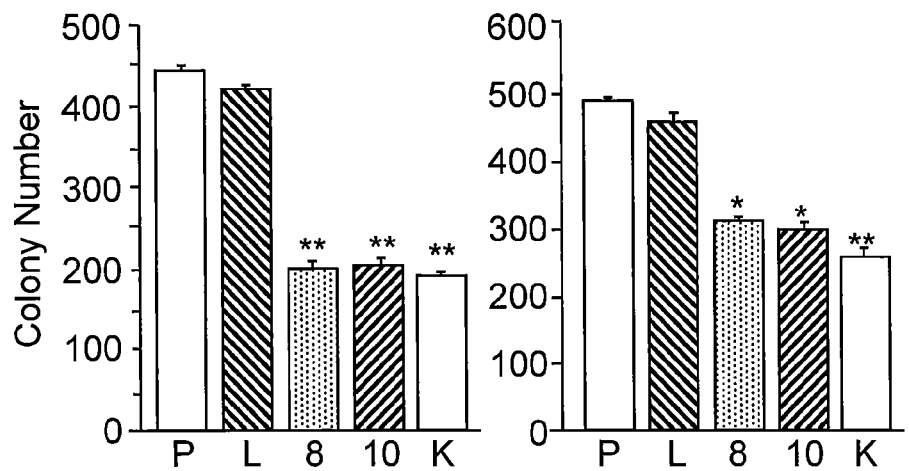
In FIG. 1B, results shown depict when anchorage-independent growth was determined in soft agar. Data are the means±SE of triplicate determinations from three independent experiments. p<0.01 when compared with Luc.

Cyclin D1 down-regulation was also associated with a significant inhibitory effect on cell proliferation, as determined by the MTT assay (FIG. 1a), and by a significant decrease in colony formation in soft agar (FIG. 1b). Thus, the number of colonies was decreased by 54% (p<0.01) and 53% (p<0.01) in ASPC-1 cells infected with sh8-LV and sh10-LV, respectively, and by 54% (p<0.01) following infection with both viruses. In BxPC3 cells, colony number was decreased by 34% (p<0.05) and 36% (p<0.05) following infection with sh8-LV and sh10-LV, respectively, and by 44% (p<0.01) following infection with both viruses.

Figure 1C:
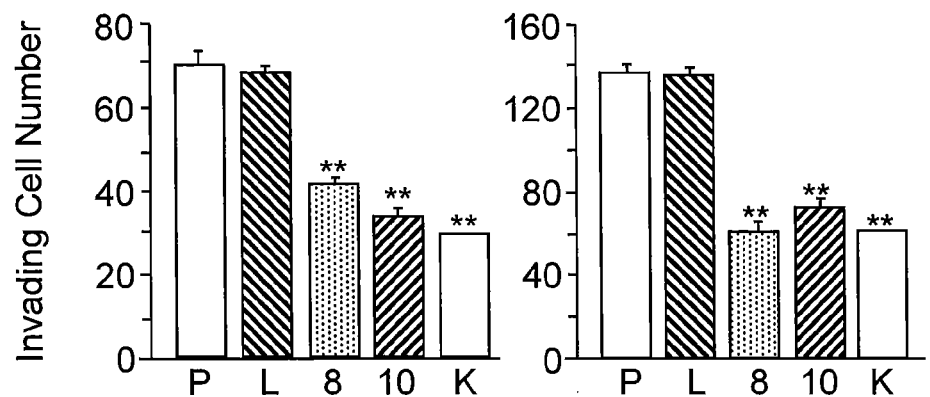
In FIG. 1C, results shown depict determination of cell invasion in Transwell chambers. Data are the means±SE of triplicate determinations from three independent experiments. **p<0.01 when compared with Luc.

The effects of cyclin D1 knock-down on cell invasion were examined next, using a Matrigel-based invasion assay. In the presence of serum (5%), cell invasion was enhanced in ASPC-1 and BxPC3 cells. In both cell lines, infection with sh8-LV, sh10-LV, or the combination, significantly attenuated the stimulatory effects of serum (FIG. 1c). In ASPC-1 cells, invasion was attenuated by 39% (sh8-LV), 50% (sh10-LV) and 57% (both), which were all statistically significant (p<0.01). In BxPC3 cells, invasion was attenuated by 54% (sh8-LV), 50% (sh10-LV) and 52% (both), which were also all statistically significant (p<0.01). Thus, in both cell lines, the combination of sh8-LV and sh10-LV was at least as effective as either lentivirus alone.

Next, the effect of cyclin D1 on the growth of established tumors was examined. To determine whether the lentivirus could efficiently infect tumors and attenuate their growth, ASPC-1 and BxPC3 cells, which express high cyclin D1 levels, were used. Tumors were generated by subcutaneous injections of ASPC-1 or BxPC3 cells (1×10$^6$ cells/injection) into the flanks of mice. Upon reaching a volume of 30-40 mm$^3$, intratumoral injections were initially performed with a GFP-expressing pll3.7 virus. After one week, strong GFP expression was observed in the dissected tumors, which was similar to that observed following injection of cancer cells that were infected ex-vivo with the GFPexpressing pll3.7 virus. These observations indicated that following injection into an established tumor, the virus itself was able to diffuse and infect cells throughout the tumor mass. The same procedure was used for testing the activity of the cyclin D1 shRNA.

Figure 2:
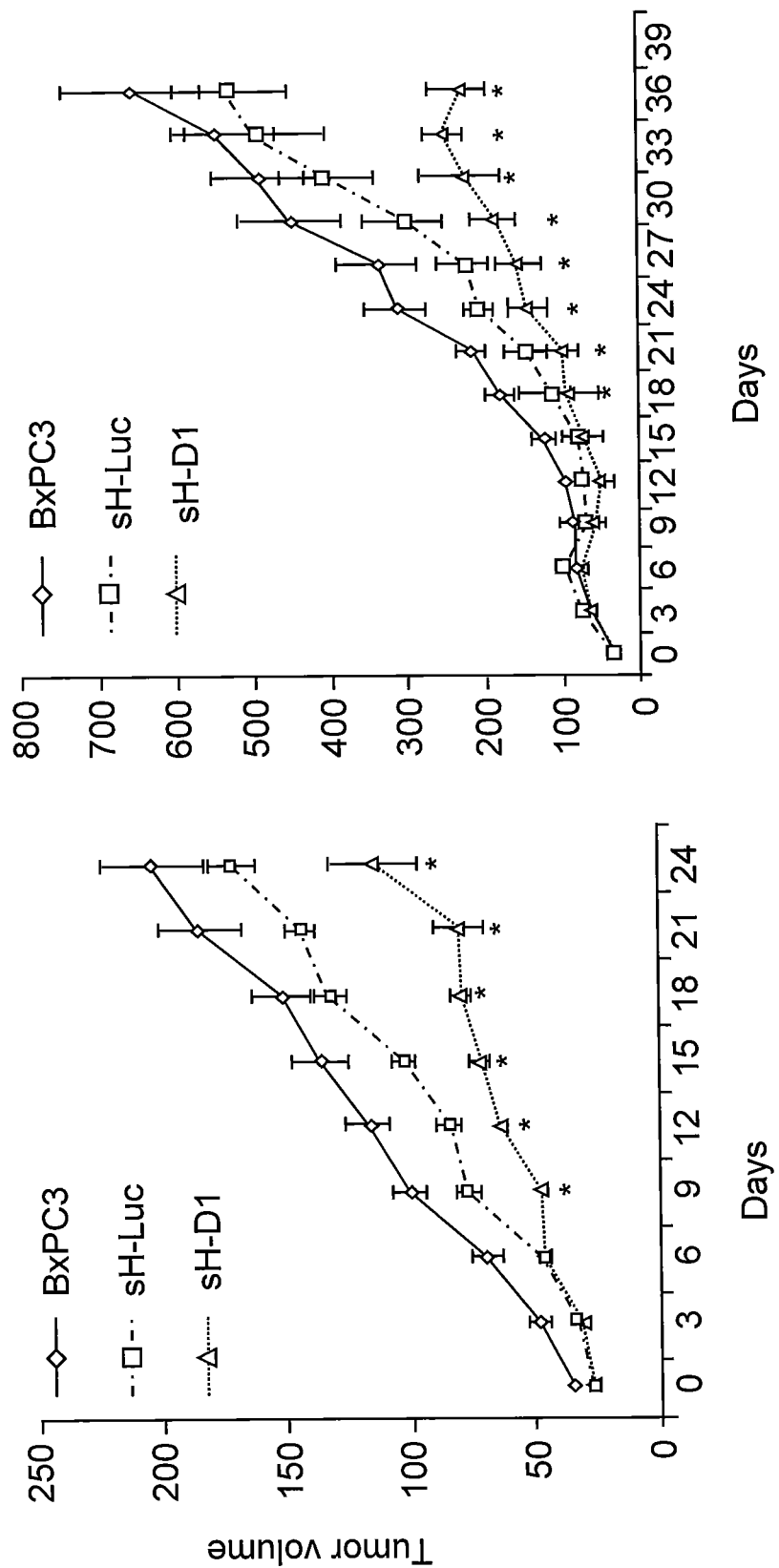
FIG. 2 depicts the effects of cyclin D1 shRNA treatment on tumor growth. ASPC-1 or BxPC3 cells were injected subcutaneously in athymic nude mice. After tumors reached a volume of 30-40 mm$^3$, they were either injected with buffer (ASPC-1) or with luciferase-directed (sh-Luc) or cyclin D1-directed (sh-D1) shRNA-lentiviruses. Tumor volumes were calculated in mm$^3$. Data are expressed as means±SEM from 8 mice in each group at each time point. *p<0.05 when compared with respective controls.

Tumors on each mouse were injected once with 50 µl of a combination of sh8-LV and sh10-LV (both shD1-LV), or with 50 µl of a control lentivirus expressing shRNA directed against luciferase (shLuc-LV). By comparison with tumors infected with shLuc-LV, the ASPC-1 and BxPC3 tumors that were infected with shD1-LV exhibited a 43% (p<0.05) and a 65% (p<0.05) decrease in volume, respectively (FIG. 2). A statistically significant difference in tumor volumes between shLuc-LV-injected tumors and shD1-LV-injected tumors was seen as early as 9 and 18 days following viral injection of ASPC-1- and BxPC3-derived tumors, respectively. Moreover, the subsequent growth of all shD1-LV-injected tumors remained significantly attenuated.

Figure 3:
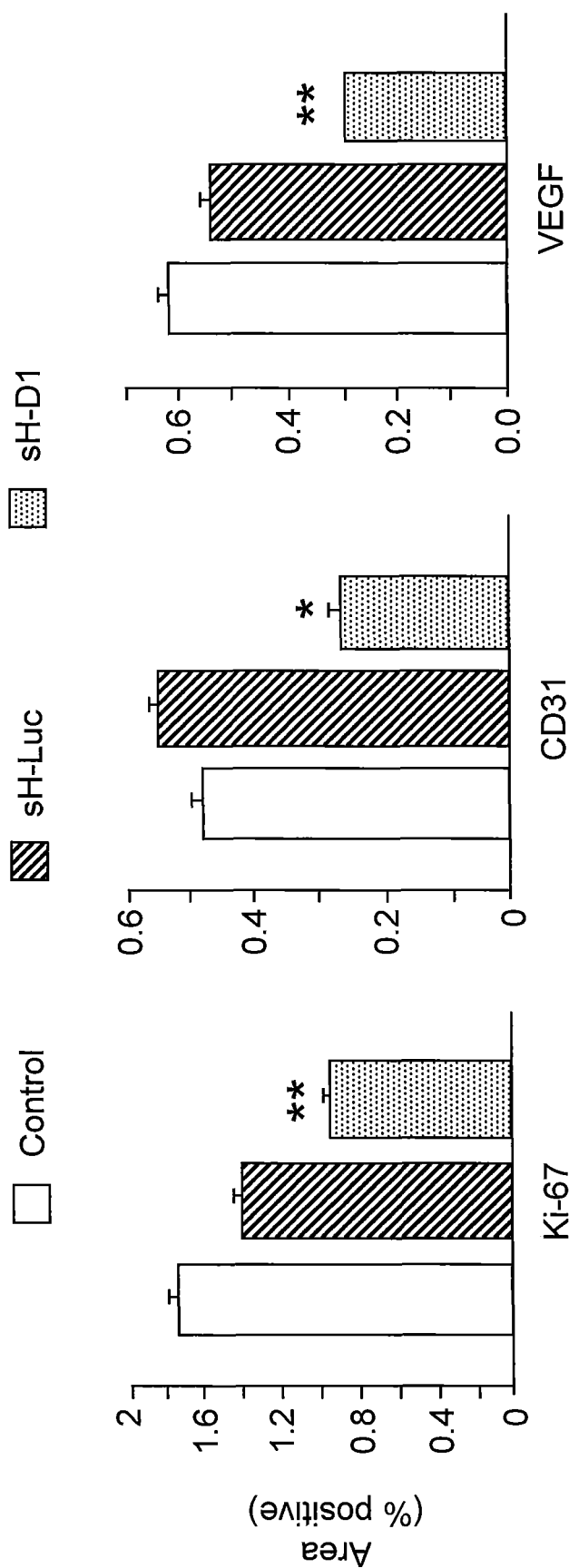
FIG. 3 depicts the effects of cyclin D1 shRNA on proliferation and angiogenesis in APSC-1-derived tumors. The results shown are the quantitative morphometry of tumors for Ki-67, CD31, and VEGF immunoreactivity. Data are the means±SEM from three tumors/group, with 10 random fields analyzed for each tumor. *P<0.05, **p<0.01 when compared with respective controls.
Figure 4:
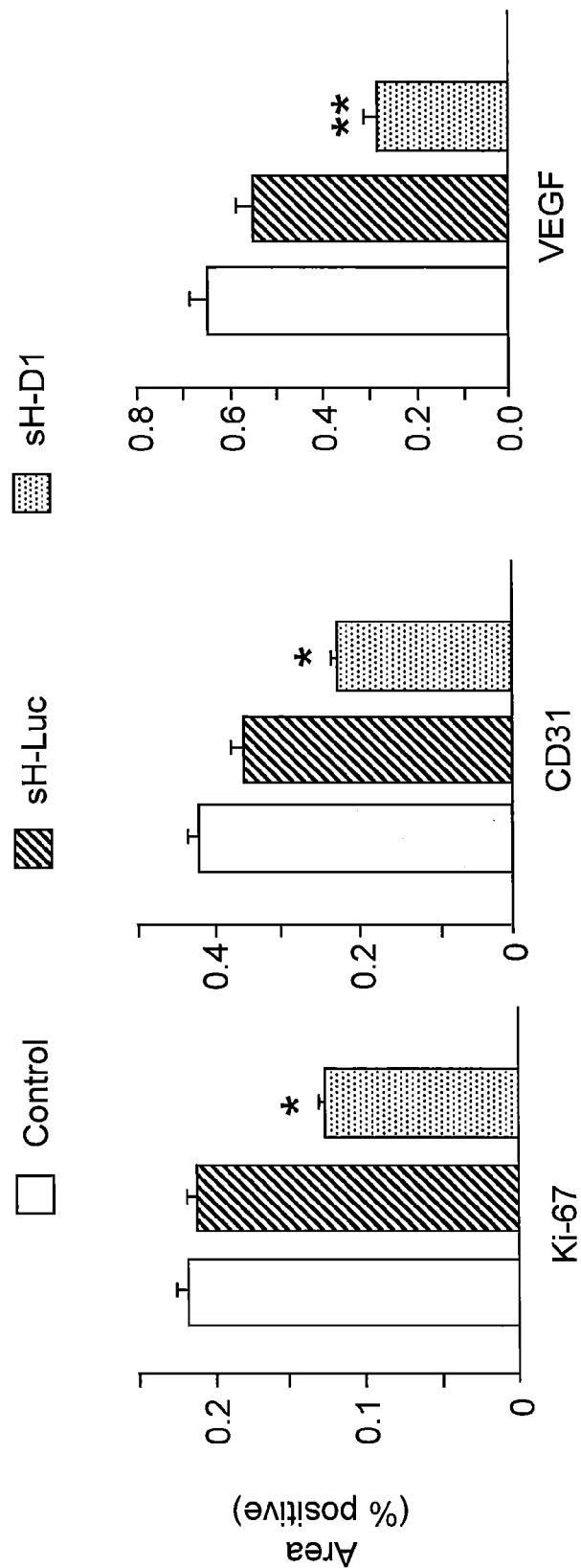
FIG. 4 depicts the effects of cyclin D1 shRNA treatment on cell proliferation and angiogenesis in BxPC3-derived tumors. The results shown are quantitative morphometry of tumors for Ki-67, CD31, and VEGF immunoreactivity. Data are the means±SEM from three tumors/cell line/group. *P<0.05, **p<0.01 when compared with respective controls.

The ASPC-1-derived tumors injected with shD1-LV exhibited a 42% decrease (p<0.01) in Ki-67 immunoreactivity, a marker of cell proliferation, and a 68% decrease (p<0.05) in CD31 immunoreactivity, an endothelial cell marker (FIG. 3). Similarly, the BxPC3-derived tumors exhibited a 32% decrease (p<0.05) in Ki-67 immunoreactivity and a 45% decrease (p<0.05) in CD31 immunoreactivity (FIG. 4). In addition, VEGF immunoreactivity was decreased by 52% (p<0.01) and 59% (p<0.01) in ASPC-1- and BxPC3-derived tumors (FIGS. 3 and 4).

Lentiviruses are a subclass of retroviruses that allow for efficient gene transduction into cells and tissues, infecting both proliferating and non-proliferating cells, and resulting in stable integration of specific genes into the cellular genome (Zufferey, R. et al. 1998. *J. Virol.* 72:1446-1452). In contrast to adenoviruses, lentiviruses do not trigger a potentially dangerous immune response. They are ideally suited, therefore, for use in silencing strategies in cancer cells. In the present invention it has been shown that a single exposure of ASPC-1 and BxPC3 human pancreatic cancer cell lines to lentiviruses encoding two different specific shRNA targeting cyclin D1 (sh8-LV and sh10-LV) resulted in stable integration of the virus and high level of expression of the shRNAs, along with subsequent marked reduction in cyclin D1 protein levels. Thus, lentiviral delivery of shRNA is an efficient way to markedly down-regulate cyclin D1 in pancreatic cancer cells.

The present invention is a method for inhibiting pancreatic tumor cell growth by contacting tumor cells with lentiviruses incorporating, and capable of expressing, cyclin D1 shRNA. Without being limited by theory, the cyclin D1 expression is inhibited by the shRNA of the invention by impeding any steps in the replication, transcription, splicing or translation of the cyclin D1 gene. The sequence of mammalian cyclin D1 is well-known in the art and disclosed in GENBANK Accession Nos. NM_053056 (human), NM_007631 (mouse) and NM_171992 (rat).

To inhibit the synthesis or expression of cyclin D1 means impeding, slowing or preventing one or more steps by which the end-product protein encoded by the cyclin D1 gene is synthesized. Typically, the inhibition involves blocking one or more steps in the gene's replication, transcription, splicing or translation through the recognition of a target site located within the gene sequence based on sequence complementation. In a specific embodiment, inhibition of cyclin D1 reduces the amount of cyclin D1 protein in a cell by greater than about 20, 30, 40, 50, 60, 70, or 80 percent. The amount of cyclin D1 can be determined by well-known methods including, but are not limited to, northern blot analysis, RT-PCR, densitometry, fluorometry, radiography, luminometry, antibody-based methods and activity measurements.

In particular embodiments of the invention, a sequence is complementary when it hybridizes to its target sequence under stringent conditions. In general, for complementary sequences to hybridize under stringent conditions, said sequences are at least 60, 70, 80, or 90 percent identical to each other. Such stringent conditions are known to those skilled in the art, and can be found, for example, in Current Protocols in Molecular Biology, John Wiley & Sons, N.Y. (1989), 6.3.1-6.3.6. Another example of stringent hybridization conditions is hybridization of the nucleotide in 6× sodium chloride/sodium citrate (SSC) at about 45° C., followed by 0.2×SSC, 0.1% SDS at 50-65° C. Another example of stringent hybridization conditions is hybridization in 6× sodium chloride/sodium citrate (SSC) at about 45° C., followed by one or more washes in 0.2×SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Alternatively, a stringent hybridization condition is hybridization in 6× sodium chloride/sodium citrate (SSC) at about 45° C., followed by one or more washes in 0.2×SSC, 0.1% SDS at 65° C. Another alternative example of stringent hybridization condition is 0.5 M sodium phosphate, 7% SDS at 65° C., followed by one or more washes at 0.2× SSC, 1% SDS at 65° C.

Depending on the conditions of binding, a sequence complementary to a target sequence within the cyclin D1 nucleic acid sequences need not be 100 percent identical to the target sequence. For example, a sequence can be complementary to its target sequence when at least about 70, 80, 90, or 95 percent of its nucleotides bind via matched base pairings with nucleotides of the target sequence. However, in the present invention it is desirable to achieve cyclin D1-specific binding; therefore, a sequence complementary to a target sequence should have limited complementary with other sequences in the genome. Sequence complementarity and specificity can be determined empirically using standard methods such as sequence comparisons (e.g., BLAST, DIALIGN, CLUSTALW) or experimentally (e.g., Southern blot analysis under stringent conditions).

In accordance with the present invention, the expression of cyclin D1 is inhibited by the use of an RNA interference technique referred to as RNAi. RNAi allows for the selective knockout of a target gene in a highly effective and specific manner. This technique involves introducing into a cell double-stranded RNA (dsRNA), having a sequence corresponding to the exon portion of the target gene. The dsRNA causes a rapid destruction of the target gene's mRNA. See, e.g., Hammond, et al. (2001) *Nature Rev. Gen.* 2:110-119; Sharp (2001) *Genes Dev.* 15:485-490.

Procedures for using RNAi technology are described by, for example, Waterhouse, et al. (1998) *Proc. Natl. Acad. Sci. USA* 95(23):13959-13964. A cyclin D1 short interfering RNA (siRNA) denotes a small interfering RNA that has a sequence complementary to a sequence within the cyclin D1 gene. Typically, siRNAs are about 20 to 23 nucleotides in length. The cyclin D1 target sequence that binds the siRNA can be selected experimentally or empirically. For example, empirical observations have indicated that shRNA oligonucleotides targeting the transcriptional start site of the target gene (Hannon (2002) Nature 418:244-51) or targeting the 3' untranslated region of the mRNA (He and Hannon (2004) Nature 5:522-531) are more effective at blocking gene expression. Further, siRNA target sites in a gene of interest are selected by identifying an AA dinucleotide sequence, typically in the coding region, and not near the start codon (within 75 bases) as these may be richer in regulatory protein binding sites which can interfere with binding of the siRNA (see, e.g., Elbashir, et al. (2001) *Nature* 411: 494-498). The subsequent 19-27 nucleotides 3' of the AA dinucleotide can be included in the target site and generally have a G/C content of 30-50%.

RNAi can be performed, for example, using chemically-synthesized RNA. Alternatively, as disclosed herein, suitable expression vectors are used to transcribe such RNA either in vitro or in vivo. In vitro transcription of sense and antisense strands (encoded by sequences present on the same vector or on separate vectors) can be effected using for example T7 RNA polymerase, in which case the vector can contain a suitable coding sequence operably-linked to a T7 promoter. The in vitro-transcribed RNA can, in certain embodiments, be processed (e.g., using RNase III) in vitro to a size conducive to RNAi. The sense and antisense transcripts are combined to form an RNA duplex which is introduced into a target cell of interest. Other vectors can be used, which express small hairpin RNAs (shRNAs) which can be processed into siRNA-like molecules. Various vector-based methods are described in, for example, Brummelkamp, et al. (2002) *Science* 296(5567): 550-3; Lee, et al. (2002) *Nat. Biotechnol.* 20(5):500-5; Miyagashi and Taira (2002) *Nat. Biotechnol.* 20(5):497-500; Paddison, et al. (2002) *Proc. Natl. Acad. Sci. USA* 99(3):1443-8; Paul, et al. (2002); and Sui, et al. (2002) *Proc. Natl. Acad. Sci. USA* 99 (8):5515-20. According to the particular embodiments of the present invention, the shRNA molecule is expressed using a lentivirus-based expression system. Such lentivirus systems are known in the art and available from sources such as Dharmacon (Lafayette, Colo.). Kits for production of dsRNA for use in RNAi are also available commercially, e.g., from New England Biolabs, Inc. and Ambion Inc. (Austin, Tex., USA). Methods of transfection of dsRNA or plasmids engineered to make dsRNA are routine in the art.

Exemplary siRNA molecules and their corresponding shRNA molecules targeting the coding region of murine cyclin D1 are listed in Table 1.

TABLE 1

| Molecule | Sequence (5'->3') | SEQ ID NO: |
|---|---|---|
| siRNA 8 | CCGAGAAGCTGTGCATCTATT | 1 |
| sh8-LV | | |
| sense | TCCGAGAAGCTGTGCATCTATTTTCAAGAGAAATAGATGCACAGCTTCTCGGTTTTTC | 2 |
| antisense | TCGAGAAAAAACCGAGAAGCTGTGCATCTATTTCTCTTGAAAATAGATGCACAGCTTCTCGGA | 3 |
| siRNA 10 | ACAACTTCCTGTCCTACTATT | 4 |
| sh10-LV | | |
| sense | TACAACTTCCTGTCCTACTATTTTCAAGAGAAATAGTAGGACAGGAAGTTGTTTTTTC | 5 |
| antisense | TCGAGAAAAAACAACTTCCTGTCCTACTATTTCTCTTGAAAATAGTAGGACAGGAAGTTGTA | 6 |

Examples of shRNA molecules targeting human cyclin D1 are listed in Table 2.

TABLE 2

| Target Start Position* | Region | shRNA molecule upper - sense, 5'-3' lower - antisense, 3'-5' | SEQ ID NO: |
|---|---|---|---|
| 3665 | 3'UTR | TGGAATAGCTTCTGGAATT | 7 |
| | | ACCTTATCGAAGACCTTAA | 8 |
| 2771 | 3'UTR | AGGCATGGGTGCAAGGAAA | 9 |
| | | TCCGTACCCACGTTCCTTT | 10 |
| 643 | ORF | TGAACAAGCTCAAGTGGAA | 11 |
| | | ACTTGTTCGAGTTCACCTT | 12 |
| 2121 | 3'UTR | TCCAATAGGTGTAGGAAAT | 13 |
| | | AGGTTATCCACATCCTTTA | 14 |
| 1305 | 3'UTR | TAAAAGAGAGAGAGAGAAA | 15 |
| | | ATTTTCTCTCTCTCTCTTT | 16 |
| 1934 | 3'UTR | AAGACGAAATAGTGACATA | 17 |
| | | TTCTGCTTTATCACTGTAT | 18 |
| 2716 | 3'UTR | ACACAAAGACATTGATTCA | 19 |
| | | TGTGTTTCTGTAACTAAGT | 20 |
| 610 | ORF | CCGAGGAGCTGCTGCAAAT | 21 |
| | | GGCTCCTCGACGACGTTTA | 22 |
| 712 | ORF | TGCCAGAGGCGGAGGAGAA | 23 |
| | | ACGGTCTCCGCCTCCTCTT | 24 |
| 1189 | 3'UTR | TTTGATACCAGAAGGGAAA | 25 |
| | | AAACTATGGTCTTCCCTTT | 26 |
| 1448 | 3'UTR | GAATAGGCATTAACACAAA | 27 |
| | | CTTATCCGTAATTGTGTTT | 28 |
| 1564 | 3'UTR | TTAAAGTAGAAGAGGGTTT | 29 |
| | | AATTTCATCTTCTCCCAAA | 30 |
| 2936 | 3'UTR | GCAAGAGTGTGGAGGCTGA | 31 |
| | | CGTTCTCACACCACCGACT | 32 |
| 4051 | 3'UTR | GGGCACAAGTCCTGGATGT | 33 |
| | | CCCGTGTTCAGGACCTACA | 34 |
| 4222 | 3'UTR | CGGCATGTTTCCAGCAGAA | 35 |
| | | GCCGTACAAAGGTCGTCTT | 36 |
| 910 | ORF | CCAGAGTGATCAAGTGTGA | 37 |
| | | GGTCTCACTAGTTCACACT | 38 |
| 1359 | 3'UTR | GGAGGAGGGTTGTGCTACA | 39 |
| | | CCTCCTCCCAACACGATGT | 40 |

*With reference to GENBANK Accession No. NM_053056.
UTR, untranslated region; ORF, open reading frame.

As will be appreciated by one skilled in the art, additional nucleotides can be added to the 5' or 3' ends of the sequences listed in Table 2 in order to facilitate synthesis, cloning, and/or specificity.

The data showed that cyclin D1 down-regulation was associated with decreased cell proliferation, attenuated anchorage-independent growth, and blunted invasiveness in vitro. This is the first direct demonstration that cyclin D1 promotes invasion in pancreatic cancer cells. It is known that patients with cyclin D1-positive pancreatic tumors tend to experience perineural and lymphatic invasion more often than patients with cyclin D1-negative tumors (Lebe, B. et al. 2004. *Pathol. Res. Pract.* 200:389-396; Sutherland, R. L. and E. A. Musgrove. 2002. *Breast Cancer Res.* 4:14-17). Therefore, the current data indicate that cyclin D1 may contribute to the invasiveness and metastatic potential of pancreatic cancer cells.

The present invention is also a method of treating pancreatic cancer in patients which comprises administering to a patient with pancreatic cancer a cyclin D1 shRNA lentivirus. Direct injection of the recombinant lentivirus was performed in established tumors. A single injection of the recombinant lentivirus was sufficient to inhibit the growth of established xenografts arising from either ASPC-1 or BxPC3 cells, indicating that down-regulation of cyclin D1 by the shRNA lentiviral strategy resulted in a sustained biological effect in vivo. This conclusion is also supported by the observation that Ki-67 staining was significantly decreased in these tumors. Inasmuch as Ki-67 is a marker of actively proliferating cells, the results indicate that cyclin D1 levels directly affect proliferation status in vivo. This decrease in proliferation is consistent with the known effects of cyclin D1 on the cell cycle, with the in vitro observations with respect to cell growth, as well as with the observation that cyclin D1 antisense expression can block the mitogenic action of EGF, FGF-2 and IGF-I in pancreatic cancer cells (Kornmann, M. et al. 1998. *J. Clin. Invest.* 101:344-352).

The results also showed that down-regulation of cyclin D1 was also associated with a significant attenuation in tumor angiogenesis, as evidenced by decreased CD31 immunoreactivity and measured by quantitative morphometry. Given the finding that VEGF levels were decreased in these tumors, silencing cyclin D1 may have led to decreased VEGF expression, which may have contributed to decreased tumor angiogenesis. In support of this conclusion, cyclin D1 down-regulation in a colorectal cancer cell line resulted in lower levels of VEGF expression in vitro, which was associated with decreased tumor angiogenesis in vivo (Yasui, M. et al. 2006. *Clin. Cancer Res.* 12:4720-4729). Alternatively, the intra-tumoral injection of the cyclin D1 shRNA lentiviruses may have led to direct down-regulation of cyclin D1 in tumor endothelial cells and a direct suppressive effect on angiogenesis in addition to the lowered expression of VEGF. Irrespective of the mechanism, given the importance of tumor angiogenesis in PDAC (Fukasawa, M. and M. Korc. 2004. *Clin. Cancer Res.* 10:3327-3332), the results indicate that targeting cyclin D1 in PDAC may have the additional benefit of suppressing angiogenesis in this malignancy.

In one embodiment, the recombinant cyclin D1 shRNA lentiviruses of the present invention may be delivered by endoscopic ultrasonography into established tumors in patients with PDAC, thereby yielding a novel therapeutic approach for this deadly malignancy. Such an approach may have multiple beneficial effects. Increased cyclin D1 expression is observed relatively early during tumorigenesis, in pre-malignant lesions termed Pancreatic Intraepithelial Neoplasia (PanIN). This suggests that targeting cyclin D1 could prevent the progression toward higher grade lesions and cancer. This is a potentially important aspect of such therapy since the presence of PanIN lesions in the vicinity of the tumor resection margins may serve as a source for cancer recurrence in PDAC. Additionally, cyclin D1 is required for carcinogenesis in some cancer models (Sutherland, R. L. and E. A. Musgrove. 2002. *Breast Cancer Res.* 4:14-17). Therefore, targeting cyclin D1 may block the actions of oncogenic Kras, which is commonly mutated in PDAC, and the actions of multiple tyrosine kinase receptors which are often overexpressed in PDAC 5. Yet another possible benefit is seen when it is considered that PDAC is characterized by the presence of an abundant stroma that contains proliferating cancer associated fibroblasts and pancreatic stellate cells, and this stroma has been proposed to confer a growth advantage to pancreatic cancer cells within the tumor mass (Korc, M. 2007. *Am. J. Surg.* 194:S84-S86). Direct injections of the virus into the pancreatic tumor mass would result in a down regulation of cyclin D1 in non cancer cells as well, which would suppress the proliferation of stromal elements. Finally, suppression of cyclin D1 levels could result in decreased angiogenesis through direct actions on the endothelial cells, and, indirectly, by decreasing VEGF expression.

Yet another contemplated advantage of the use of the method of the present invention is as adjunct treatment during chemotherapy. Elevated cyclin D1 levels contribute to the chemoresistance of pancreatic cancer cells, as shown by the increased chemosensitivity to cis-platinum of PDAC cells when cyclin D1 expression is inhibited (Kornmann, M. et al. 1999. *Cancer Res.* 59:3505-3511). Therefore, targeting cyclin D1 may allow for suppression of tumor growth and angiogenesis, while allowing for more effective responses to chemotherapeutic agents. Taken together, these observations raise the possibility that intra-tumoral injections of viruses targeting cyclin D1, in conjunction with standard chemotherapy, could provide a novel therapeutic approach in PDAC. As a result, the lentivirus-based cyclin D1 shRNA compositions used in the method of the present invention can be administered alone or in combination with other agents which are used to treat pancreatic cancer including, but not limited to, surgery, radiation therapy, or chemotherapy, e.g., with gemcitabine, oxaliplatin, erlotinib, bevacizumab, trasduzumab, mitoxantrone, fluoruracil, sorafenib, sunitimib, and lapatinib The exact dosage of the lentivirus-based cyclin D1 shRNA compositions will be dependent on factors related to the subject that requires treatment. Dosage can be adjusted to provide sufficient levels of the compounds to maintain the desired effect of inhibiting tumor cells growth. Factors which can be taken into account include the severity of the existing symptoms, general health of the subject, age, weight, and gender of the subject and general susceptibility to motion sickness. When used in combination with other agents, the dosage of the other agent used will be dependent on the agent and the formulation thereof.

The invention is described in greater detail by the following non-limiting examples.

Example 1

Cell Growth and Invasion Assays

ASPC-1 and BxPC3 human pancreatic cancer cell lines from ATCC (Manassas, Va.) were grown in RPMI 1640 (Mediatech Inc., Herndon, Va.). Medium was supplemented with 10% fetal bovine serum (FBS) from Omega Scientific Inc. (Tarzana, Calif.), and with 100 U/ml penicillin and 100 μg/ml streptomycin (complete medium).

Example 2

Doubling Time

To assess doubling time, cells were seeded in 6 well plates at a density of $1.0 \times 10^4$ cells/plate and doubling time was calculated over 5 days. All doubling time experiments were repeated three separate times, each time on separate days.

Example 3

3-(4,5-dimethylthiazol-2-yl)-2,5-diphenyltetrazolium bromide (MTT) growth assay Cells (3,000 per well) were plated in 96-well microtiter plates (Corning, Acton, Mass.). MTT was added to each well (final concentration 0.5 mg/ml) 72 hours later. The plates were incubated at 37° C. for 3 hours, and the medium replaced with 100 µl of acidified isopropanol followed by gentle shaking for 15 min to solubilize the formazan blue crystals. Absorbance at 570 nm was measured using a microtiter plate reader. Cell viability was expressed as the percentage of growth of parental cells. Each experimental condition was assayed in six wells, and each experiment was repeated at least three times.

Example 4

Soft Agar Assay

Soft agar assays were performed as reported previously 18. Cells ($8 \times 10^3$) were suspended in complete medium containing 0.3% agar and seeded in triplicate in 6-well plates onto a base layer of complete medium containing 1% agar. Complete medium containing 0.3% agar was added every 5 days for 15 days, and colony counting was then performed.

Example 5

Invasion Assays

Invasion assays were performed as reported previously (Neupane, D. et al. 2008. *Clin. Cancer Res.* 14:7614-7623). Briefly, cells were suspended in 500 µL RPMI with 0.1% bovine serum albumin and placed onto the upper compartment of Matrigel-coated Transwell chambers (8 µm pore size, BioCoat Matrigel Invasion Chambers; BD Biosciences). The lower compartment was filled with 750 µL RPMI with 5% serum. After 18 to 20 hours, cells on the upper surface of the filter were carefully removed with a cotton swab and the membranes were fixed in methanol. The cells that had migrated through the membrane to the lower surface of the filter were stained with toluidine blue (Fisher Scientific) and counted using a light microscope.

Example 6

Immunoblotting

Immunoblotting was done as described previously (Kleeff, J. et al. 1998. *J. Biol. Chem.* 273:7495-7500). Briefly, PVDF membranes were incubated overnight with a 1:1000 dilution of anti-cyclin D1 human anti-mouse monoclonal antibody (Cell Signaling Technology, Danvers, Mass.), washed, and incubated for 30 minutes with a secondary horseradish peroxidase-conjugated antibody. Bound antibodies were visualized using enhanced chemiluminescence (Pierce, Rockford, Ill.). To confirm equal loading of lanes, membranes were stripped for 30 minutes at 50° C. in buffer containing 2% SDS, 62.5 mM Tris (pH 6.7), and 100 mM 2-mercaptoethanol and blotted with a 1:10,000 dilution of a rat anti-tubulin antibody (Abcam, Cambridge, Mass.).

Example 7 siRNA Transient Transfection and Lentivirus shRNA Gene Transduction siRNA sequences directed against human cyclin D1 (Dharmacon, Lafayette, Colo.) were initially transfected into ASPC-1 cells using Jet PEI (Qbiogene, Solon, Ohio) according to the manufacturer's protocol. Oligonucleotides corresponding to the shRNA sequence of interest were annealed and cloned into the lentivirus vector, pLentiLox 3.7 (pll3.7) 7 (Addgene, Cambridge, Mass.). Virus stocks were prepared by co-transfecting pll3.7 with three packaging plasmids (pM-DLg/pRRE, CMV-VSVG and RSV-Rev) into 293T cells 21. The viral supernatants were harvested 36-48 hours later, filtered and centrifuged (90 min at 25,000×g). Viral titers were determined by fluorescence-activated cell sorting (FACS) analysis.

Example 8

In Vivo Tumorigenicity Assay

To assess the effects of cyclin D1 suppression on established tumors, 24 mice were injected subcutaneously into the dorsal flank area with 200 µl containing $1 \times 10^6$ ASPC-1 cells. Separately, 24 mice were similarly injected with 200 µl containing $1 \times 10^6$ BxPC3 cells. The mice were divided randomly into three groups of 8 mice per cell line. Once tumors reached a volume of 30-40 mm3 (usually 8-10 days after injection of the cells), the tumors were injected with 50 µL (4.107 viral particles) of Optimem (Invitrogen, Carlsbad, Calif.), with virus containing the shRNA against luciferase, or with virus containing the shRNA against cyclin D1. The tumors were measured every three days. Tumor volumes were calculated as $\pi/4 \times width \times height \times length$ of the tumor (Rowland-Goldsmith, M. A. et al. 2002. *Mol. Cancer. Ther.* 1:161-167). When the tumor diameter reached 15 mm, the mice were sacrificed.

Example 9

Immunohistochemistry

Following rapid tumor removal, tissues were cryo-embedded in cryo-OCT compound (Fisher Scientific, Pittsburgh, Pa.). All immunohistochemistry experiments were performed as previously described (Fukasawa, M. et al. 2004. *Clin. Cancer Res.* 10:3327-3332). The following antibodies were used: a rabbit polyclonal anti-Ki-67 (Abcam, Cambridge, Mass.; 1:50 dilution) antibody to assess proliferation, a rat antimouse monoclonal antibody targeting CD31 as an endothelial cell marker (PharMingen, San Jose, Calif.; 1:100 dilution), and a polyclonal anti-VEGF (Santa Cruz, Santa Cruz Calif.; 1:50 dilution) antibody. Quantitative morphometric analysis of Ki-67, CD31 and VEGF positive cells in tumor samples was carried out as previously reported (Luo, J. et al. 2001. *Int. J. Cancer* 92:361-369). Briefly, 10 areas/slide were captured using Olympus DP70 camera (100× magnification) and quantified with the Image-Pro plus program (Version 4.51, Media cybernetics, L.P., Silver Spring, Md.). Three tumors per group were analyzed. Blood vessel densities were calculated as the ratio of CD31 positive areas to the total area of the image, whereas proliferation was calculated as the ratio of Ki-67 area to total cell area.

What is claimed is:

1. A method for inhibiting growth of pancreatic cancer cells comprising contacting pancreatic cancer cells with a lentivirus construct expressing a cyclin D1 short hairpin RNA molecule so that growth of pancreatic cancer cells is inhibited, and wherein said cyclin D1 short hairpin RNA molecule comprises SEQ ID NO: 2, SEQ ID NO: 3, SEQ ID NO: 5 or SEQ ID NO: 6.

2. The method of claim 1, wherein said pancreatic cancer cells are pancreatic ductal adenocarcinoma cells.

3. The method of claim 1, wherein said lentivirus construct is injected directly into the cancer cells.

4. A method for decreasing tumor angiogenesis comprising contacting pancreatic tumor cells with a lentivirus construct expressing a cyclin D1 short hairpin RNA molecule so that tumor angiogenesis is decreased, and wherein said cyclin D1 short hairpin RNA molecule comprises SEQ ID NO: 2, SEQ ID NO: 3, SEQ ID NO: 5 or SEQ ID NO: 6.

5. The method of claim 4, wherein said tumor cells are pancreatic ductal adenocarcinoma cells.

6. The method of claim 4, wherein said lentivirus construct is injected directly into the tumor cells.

7. A method for treating pancreatic cancer comprising administering to a patient diagnosed with pancreatic cancer a replicative-defective lentivirus construct expressing a cyclin D1 short hairpin RNA molecule in admixture with a pharmaceutically acceptable vehicle, and wherein said cyclin D1 short hairpin RNA molecule comprises SEQ ID NO: 2, SEQ ID NO: 3, SEQ ID NO: 5 or SEQ ID NO: 6.

8. The method of claim 7, wherein said replication-defective lentivirus construct is injected directly into pancreatic tumor cells of the patient diagnosed with pancreatic cancer.

* * * * *

SEQUENCE LISTING

<160> NUMBER OF SEQ ID NOS: 40

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
ccgagaagct gtgcatctat t                                      21

<210> SEQ ID NO 2
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 2
tccgagaagc tgtgcatcta ttttcaagag aaatagatgc acagcttctc ggttttttc    59

<210> SEQ ID NO 3
<211> LENGTH: 63
<212> TYPE: DNA
<213> ORGANISM: Artificial Sequence
<220> FEATURE:
<223> OTHER INFORMATION: Synthetic oligonucleotide

<400> SEQUENCE: 3
tcgagaaaaa accgagaagc tgtgcatcta tttctcttga aaatagatgc acagcttctc    60
gga                                                                 63

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
acaacttcct gtcctactat t                                      21

<210> SEQ ID NO 5
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 5
tacaacttcc tgtcctacta ttttcaagag aaatagtagg acaggaagtt gttttttc     59

<210> SEQ ID NO 6
<211> LENGTH: 63
<212> TYPE: DNA
<213> ORGANISM: Artificial Sequence
<220> FEATURE:
<223> OTHER INFORMATION: Synthetic oligonucleotide

<400> SEQUENCE: 6
tcgagaaaaa acaacttcc tgtcctacta tttctcttga aaatagtagg acaggaagtt    60
gta                                                                 63

```
<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
tggaatagct tctggaatt                                                   19

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 8
accttatcga agaccttaa                                                   19

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
aggcatgggt gcaaggaaa                                                   19

<210> SEQ ID NO 10
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 10
tccgtaccca cgttccttt                                                   19

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 11
tgaacaagct caagtggaa                                                   19

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12
acttgttcga gttcacctt                                                   19

<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide
```

```
<400> SEQUENCE: 13
tccaataggt gtaggaaat                                              19

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 14
aggttatcca catccttta                                              19

<210> SEQ ID NO 15
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 15
taaaagagag agagagaaa                                              19

<210> SEQ ID NO 16
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 16
attttctctc tctctcttt                                              19

<210> SEQ ID NO 17
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 17
aagacgaaat agtgacata                                              19

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 18
ttctgcttta tcactgtat                                              19

<210> SEQ ID NO 19
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 19
acacaaagac attgattca                                              19

<210> SEQ ID NO 20
<211> LENGTH: 19
<212> TYPE: DNA
```

<213> ORGANISM: Artificial Sequence
<220> FEATURE:
<223> OTHER INFORMATION: Synthetic oligonucleotide

<400> SEQUENCE: 20
tgtgtttctg taactaagt                                                19

<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 21
ccgaggagct gctgcaaat                                                19

<210> SEQ ID NO 22
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 22
ggctcctcga cgacgttta                                                19

<210> SEQ ID NO 23
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 23
tgccagaggc ggaggagaa                                                19

<210> SEQ ID NO 24
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 24
acggtctccg cctcctctt                                                19

<210> SEQ ID NO 25
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 25
tttgatacca gaagggaaa                                                19

<210> SEQ ID NO 26
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 26
aaactatggt cttcccttt                                                19

```
<210> SEQ ID NO 27
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 27
gaataggcat taacacaaa                                                    19

<210> SEQ ID NO 28
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 28
cttatccgta attgtgttt                                                    19

<210> SEQ ID NO 29
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 29
ttaaagtaga agagggttt                                                    19

<210> SEQ ID NO 30
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 30
aatttcatct tctcccaaa                                                    19

<210> SEQ ID NO 31
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 31
gcaagagtgt ggaggctga                                                    19

<210> SEQ ID NO 32
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 32
cgttctcaca ccaccgact                                                    19

<210> SEQ ID NO 33
<211> LENGTH: 19
<212> TYPE: DNA
<213> ORGANISM: Artificial Sequence
<220> FEATURE:
<223> OTHER INFORMATION: Synthetic oligonucleotide
```

<400> SEQUENCE: 33
gggcacaagt cctggatgt                                                    19

<210> SEQ ID NO 34
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 34
cccgtgttca ggacctaca                                                    19

<210> SEQ ID NO 35
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 35
cggcatgttt ccagcagaa                                                    19

<210> SEQ ID NO 36
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 36
gccgtacaaa ggtcgtctt                                                    19

<210> SEQ ID NO 37
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 37
ccagagtgat caagtgtga                                                    19

<210> SEQ ID NO 38
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 38
ggtctcacta gttcacact                                                    19

<210> SEQ ID NO 39
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 39
ggaggagggt tgtgctaca                                                    19

<210> SEQ ID NO 40
<211> LENGTH: 19
<212> TYPE: DNA

-continued

```
<213> ORGANISM: Artificial Sequence
<220> FEATURE:
<223> OTHER INFORMATION: Synthetic oligonucleotide

<400> SEQUENCE: 40
cctcctccca acacgatgt                                                19
```